United States Patent
Felmlee et al.

(10) Patent No.: US 9,134,393 B2
(45) Date of Patent: Sep. 15, 2015

(54) SYSTEM AND METHOD FOR IMPROVED EFFICIENCY IN MAGNETIC RESONANCE ELASTOGRAPHY

(71) Applicants: Joel P. Felmlee, Rochester, MN (US); Richard L. Ehman, Rochester, MN (US); Matthew C. Murphy, Rochester, MN (US)

(72) Inventors: Joel P. Felmlee, Rochester, MN (US); Richard L. Ehman, Rochester, MN (US); Matthew C. Murphy, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 14/049,632

(22) Filed: Oct. 9, 2013

(65) Prior Publication Data
US 2014/0107467 A1     Apr. 17, 2014

Related U.S. Application Data

(60) Provisional application No. 61/713,852, filed on Oct. 15, 2012, provisional application No. 61/729,491, filed on Nov. 23, 2012.

(51) Int. Cl.
| | |
|---|---|
| *A61B 5/055* | (2006.01) |
| *G01R 33/48* | (2006.01) |
| *A61B 8/08* | (2006.01) |
| *A61B 5/00* | (2006.01) |
| *G01R 33/563* | (2006.01) |

(52) U.S. Cl.
CPC .......... *G01R 33/4814* (2013.01); *A61B 5/0035* (2013.01); *A61B 5/055* (2013.01); *A61B 5/725* (2013.01); *A61B 5/7278* (2013.01); *A61B 8/485* (2013.01); *G01R 33/56358* (2013.01)

(58) Field of Classification Search
CPC ...... A61B 5/0035; A61B 5/055; A61B 5/725; A61B 5/7278; A61B 8/485; G01R 33/4814; G01R 33/56358
See application file for complete search history.

(56) References Cited

U.S. PATENT DOCUMENTS

| | | | |
|---|---|---|---|
| 8,030,923 B2 | 10/2011 | Yu et al. | |
| 2011/0304330 A1 | 12/2011 | Yoneda et al. | |

OTHER PUBLICATIONS

Murphy et al , "Analysis of Time Reduction Methods for Magnetic Resonance Elastography of the Brain", Magn Reson Imaging, Dec. 2010, 28(10), pp. 1514-1524.*

Caparelli, et al., k-Space Spatial Low-Pass Filters Can Increase Signal Loss Artifacts in Echo-Planar Imaging, Biomedical Signal Processing and Control, 2008, 3:107-114.

* cited by examiner

*Primary Examiner* — Ruth S Smith
(74) *Attorney, Agent, or Firm* — Quarles & Brady, LLP

(57) ABSTRACT

A system and method for generating a magnetic resonance elastography (MRE) report includes a) acquiring MRE data from a subject including positively motion encoded medical imaging data and negatively motion encoded medical imaging data and b) deriving uncorrected difference medical imaging data from the MRE data for a given slice. The method also includes c) filtering the uncorrected difference medical imaging data to create filtered medical imaging data corrected for errors associated with phase ramps occurring during gradient switching used to derive the positively motion encoded medical imaging data and negatively motion encoded medical imaging data, d) generating a corrected difference image for the given slice from the filtered medical imaging data and the uncorrected difference medical imaging data, e) repeating steps b) through d) for each slice reflected in the MRE data, and f) generating a report of elastic properties of the subject from the corrected difference image.

13 Claims, 5 Drawing Sheets

SYSTEM AND METHOD FOR IMPROVED EFFICIENCY IN MAGNETIC RESONANCE ELASTOGRAPHY

CROSS REFERENCE

This application is based on, claims the benefit of, and incorporates herein by reference in their entirety, U.S. Provisional Application Ser. No. 61/713,852, filed Oct. 15, 2012, and entitled "SYSTEM AND METHOD FOR IMPROVED EFFICIENCY IN MAGNETIC RESONANCE ELASTOGRAPHY" and U.S. Provisional Application Ser. No. 61/729,491, filed Nov. 23, 2012, and entitled "SYSTEM AND METHOD FOR IMPROVED EFFICIENCY IN MAGNETIC RESONANCE ELASTOGRAPHY."

STATEMENT REGARDING FEDERALLY SPONSORED RESEARCH

This invention was made with government support under EB001981 awarded by the National Institutes of Health. The government has certain rights in this invention.

BACKGROUND OF THE INVENTION

The field of the invention relates to magnetic resonance imaging methods and systems. More particularly, the invention relates to systems and methods for performing magnetic resonance elastography (MRE) with improved efficiency by utilizing pulse sequences that are often avoided when performing MRE because the pulse sequences, though relatively expedient by nature, can introduce substantial artifacts in elastogram images. The present invention provides systems and methods to control and overcome these drawbacks to produce clinically-useful elastogram images when using such pulse sequences.

When a substance such as human tissue is subjected to a uniform magnetic field (polarizing field $B_0$), the individual magnetic moments of the nuclear spins in the tissue attempt to align with this polarizing field, but process about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

It has been found that MR imaging can be enhanced when an oscillating stress is applied to the object being imaged in a method called MR elastography (MRE). MRE is gaining wider clinical applicability due to its ability to noninvasively and quantitatively measure tissue stiffness. MRE is a multi-step process beginning with the induction of shear waves in the tissue to be examined via an external source of vibration. The shear waves are then imaged with a phase-contrast MRI pulse sequence with motion-encoding gradients synchronized with the applied vibration. The resulting wave images of the wave motion are inverted to calculate the tissue stiffness and produce an elastogram image.

MRE is analogous to manual palpation, which has a long history in the practice of medicine as a clinical diagnostic tool for examining tissues such as the breast and thyroid for focal and diffuse diseases. In fact, MRE of the liver has already matured to a point where it is replacing needle biopsies for the diagnosis of fibrosis and cirrhosis in a growing number of clinical practices.

As generally described above, MRE utilizes the oscillating stress produced by the shear waves that propagate through the organ, or tissues to be imaged, to elicit information about tissue stiffness. Specifically, these shear waves alter the phase of the MR signals and, from this, the mechanical properties of the tissue can be determined. However, to do so, the MRI pulse sequence must be carefully timed to the oscillations generating the shear waves. That is, the wave images are calculated as the phase difference between two images that are acquired using an MRI pulse sequence. Specifically, one image is acquired during a positive motion encoding gradients and the second image is acquired during a negative motion encoding. The two motion encoding gradients are synchronized to the oscillations used to generate the shear waves.

Unfortunately, hardware or software errors in the acquisition process can result in a constant or slowly varying phase ramp that may remain in the wave image after performing the phase difference calculation. For example, some very popular and advantageous (for example, fast) pulse sequences, such as the echo-planar imaging (EPI) pulse sequence, inherently present such errors when used as part of an MRE pulse sequence. To make matters worse, in some instances, these errors can vary over time. Further still, when performing three-dimensional (3D) image processing, these errors or discontinuities can produce a high frequency artifact in the slice direction that results in an inaccurate stiffness calculation. When manifested as inaccurate stiffness calculations, such errors can undermine the clinical utility of the final elastogram image. Such erroneous stiffness calculations, in some cases, can not be readily discerned by the clinician, even when highly experienced in reading stiffness calculations or elastogram images. As such, though there are a variety of pulse sequences that are advantageously and regularly used in other MRI applications, such as the EPI pulse sequence, such pulse sequences are often foregone when performing MRE.

Therefore, it would be desirable to have a system and method for expanding the variety of pulse sequences available when performing MRE, particularly, to include pulse sequences such as EPI that are generally regarded as highly efficient and versatile.

SUMMARY OF THE INVENTION

The present invention overcomes the aforementioned drawbacks, such as phase discontinuity problems, by providing a system and method for correcting magnetic resonance elastography (MRE) data for errors associated with phase ramps induced by particular pulse sequences when used in an MRE imaging process. The data is corrected using a low-pass filter to correct a given slice of data. By correcting each slice of the data, the present invention yields substantially improved and robust data and enables the use of pulse sequences for MRE processes that might otherwise be avoided due to a propensity to yield data that is clinically unsatisfactory.

In accordance with one aspect of the present invention, a method for generating a magnetic resonance elastography (MRE) image is disclosed that includes a) positioning a subject within the MRI system and b) coupling a driver to the subject to impart oscillating energy to the subject. The method also includes c) using the MRI system and in coordination with operation of the driver, performing a pulse sequence having positive and negative motion encoded gradients to acquire positively motion encoded medical imaging data and negatively motion encoded medical imaging data from the subject. The method further includes d) transforming the positively motion encoded medical imaging data and negatively motion encoded medical imaging data for a given slice into a positively encoded medical image and a negatively encoded medical image of the subject and e) deriving a difference image from the positively encoded medical image and the negatively encoded medical image. The method includes f) transforming the difference image into difference medical imaging data, g) applying a filter to correct for errors in the difference medical imaging data associated with phase ramps during the pulse sequence and create filtered medical imaging data, and h) deriving a filtered difference image from the filtered medical imaging data. The method also includes i) generating a corrected difference image from the filtered difference image and the difference image, j) repeating steps d) through i) for each slice acquired in step c), and k) generating a report of elastic properties of the subject from the corrected difference image.

In accordance with another aspect of the invention, a method for generating a magnetic resonance elastography (MRE) report is disclosed that includes a) acquiring MRE data from a subject including positively motion encoded medical imaging data and negatively motion encoded medical imaging data and b) deriving uncorrected difference medical imaging data from the positively motion encoded medical imaging data and negatively motion encoded medical imaging data for a given slice. The method also includes c) filtering the uncorrected difference medical imaging data to create filtered medical imaging data corrected for errors associated with phase ramps occurring during gradient switching used to derive the positively motion encoded medical imaging data and negatively motion encoded medical imaging data and d) generating a corrected difference image for the given slice from the filtered medical imaging data and the uncorrected difference medical imaging data. The method further includes e) repeating steps b) through d) for each of a plurality of slices reflected in the MRE data and f) generating a report of elastic properties of the subject from the corrected difference image.

In accordance with yet another aspect of the invention, a magnetic resonance imaging (MRI) system is disclosed that includes a magnet system configured to generate a polarizing magnetic field about at least a portion of a subject and a plurality of gradient coils configured to apply a gradient field to the polarizing magnetic field. The system also includes a radio frequency (RF) system configured to apply an excitation field to the subject and acquire MR image data therefrom and a driver system configured to deliver an oscillatory stress to the subject to, thereby, direct a shear wave through the subject. The system includes a computer system programmed to control operation of the gradient coils and the driver system to coordinate characteristics of the oscillatory stress with application of the gradient field and control operation of the RF system to acquire medical imaging data from the subject. The computer system is further programmed to a) control operation of the gradient coils and the driver system to coordinate characteristics of the oscillatory stress with application of the gradient field to cycle through positively motion encoding gradients and negative motion encoding gradients and b) control operation of the RF system to acquire positively motion encoded medical imaging data and negatively motion encoded medical imaging data for a series of slices. The computer system is further programmed to c) derive a difference imaging data from the positively encoded medical imaging data and the negatively encoded medical imaging data, d) apply a filter in k-space to correct for errors in the difference medical imaging data associated with phase ramps during operation of the gradient coils and create filtered medical imaging data, and e) derive filtered difference imaging data from the filtered medical imaging data. The computer system is also programmed to f) generate a corrected difference image from the filtered difference imaging data and the difference imaging data, g) repeat steps c) through f) for each slice in the series of slices, and h) generate a report of elastic properties of the subject from the corrected difference image for each slice.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
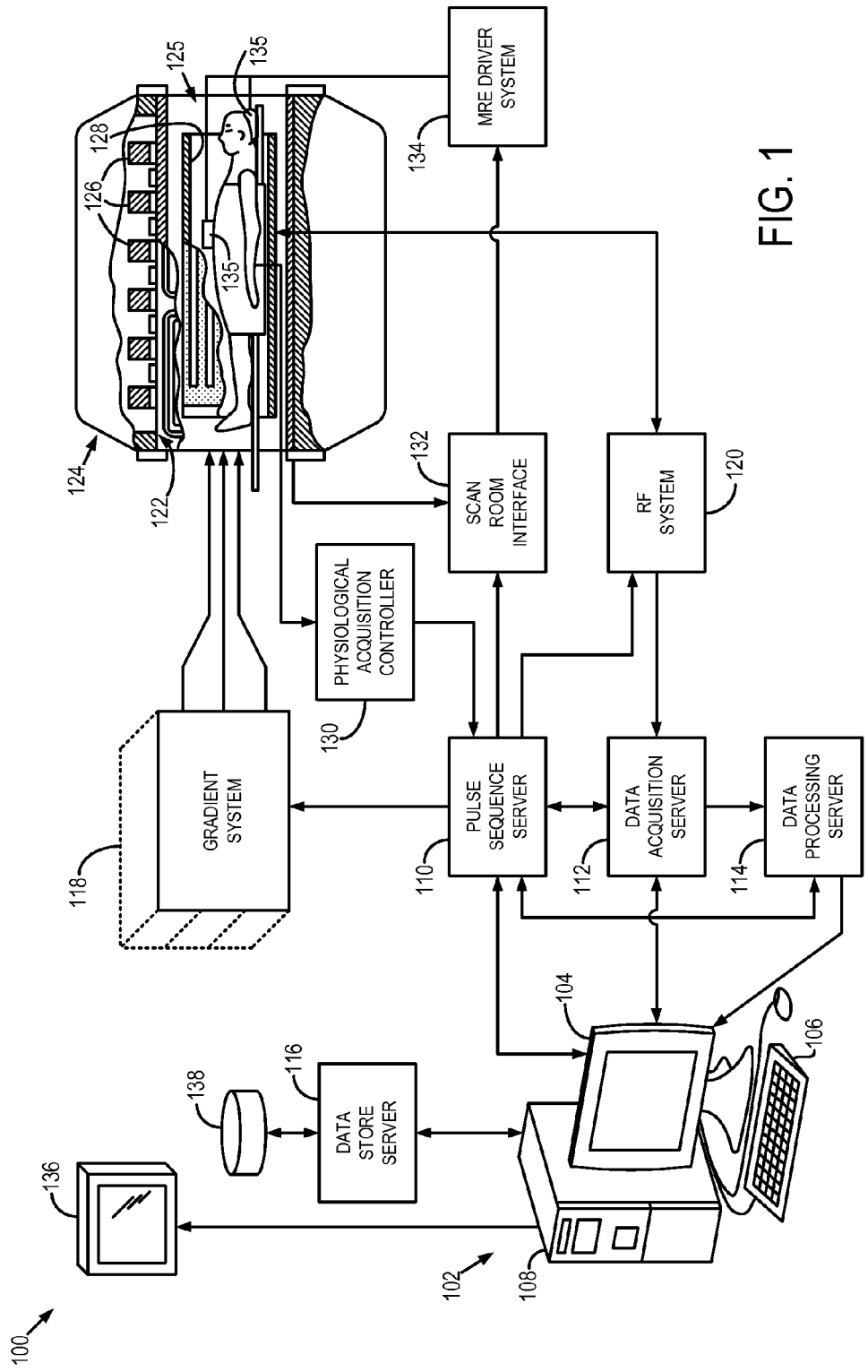
FIG. 1 is a block diagram of a magnetic resonance imaging ("MRI") system that employs the present invention.

Referring to FIG. 1, the present invention is employed in a magnetic resonance imaging ("MRI") system 100. The MRI system 100 includes a workstation 102 having a display 104 and a keyboard 106. The workstation 102 includes a processor 108, such as a commercially available programmable machine running a commercially available operating system. Though a single workstation 102 is illustrated, multiple workstations and remote computers or workstations may be included with or connected to the system 100. The system 100 may be connected to the Internet and data and control processes may be accessed from the workstation 102, from remote workstations, and/or over the Internet.

The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 extending about a bore 125 formed there through and includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad \text{Eqn. (1);}$$

and the phase of the received MR signal may also be determined:

$$\phi = \tan^{-1}\left(\frac{Q}{I}\right). \quad \text{Eqn. (2)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It may also be through the scan room interface circuit 132 that a MRE driver system 134 is coupled to the pulse sequence server 110 to, as will be described, coordinate operation of the an MRE driver 135, with the MRI system 100 to perform an MRE process.

A variety of MRE driver systems, including active and passive driver systems, are known. As illustrated, the MRE driver 135 may have various forms for use with different anatomical regions. For example, FIG. 1, for exemplary purposes only, illustrates two alternative MRE driver designs and uses. One MRE driver is illustrated for use with imaging of the abdomen and the other MRE driver is illustrated for use with imaging of the head. Various other driver configurations and designs are contemplated for use with the present invention.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Such processing may include, for example: transformation of MRE wave images into elastograms. In traditional MRE processing, complex phase difference images are calculated as the complex conjugate product of the complex positively motion encoded image and the complex negatively motion encoded image. The phase of this image is equal to the phase difference and serves as a wave image that is subjected to an inversion method to create the desired elastogram.

Figure 2:
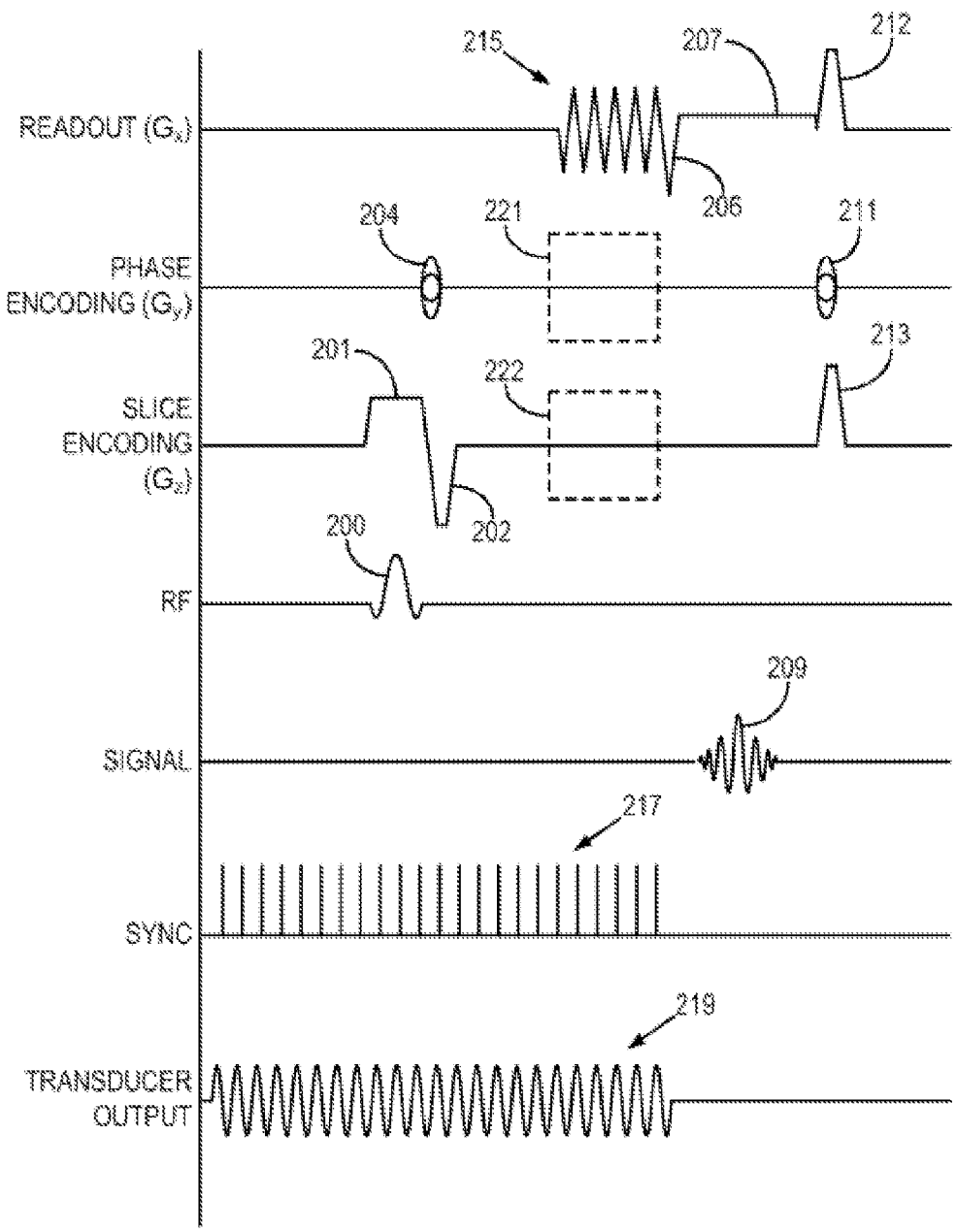
FIG. 2 is a graphic representation of an exemplary magnetic resonance elastography ("MRE") pulse sequence employed by the MRI system of FIG. 1.

Specifically, referring particularly to FIG. 2, an exemplary pulse sequence, which may be used to acquire magnetic resonance ("MR") data according to an embodiment of the present invention, is shown. The pulse sequence is fundamentally an EPI MRE pulse sequence using a gradient recalled echo. Transverse magnetization is produced by a selective 90 degree radiofrequency ("RF") excitation pulse 200 that is produced in the presence of a slice select gradient, $G_z$, pulse 201 and followed by a rephasing gradient pulse 202. A phase encoding gradient, $G_y$, pulse 204 is then applied at an amplitude and polarity determined by the view number of the acquisition. A read gradient, $G_x$, waveform is applied as a negative dephasing lobe 206, followed by a positive readout gradient pulse 207. An MR echo signal 209 is acquired after the RF excitation pulse 200 during the readout pulse 207 to frequency encode the digitized samples. The pulse sequence may be concluded with spoiler gradient pulses 212 and 213 along read and slice select axes, and a rephasing gradient pulse 211 applied along the phase encoding axis ("$G_y$-axis"). As is well known in the art, this rephasing pulse 211 has the same size and shape, but opposite polarity of the phase encoding pulse 204. The pulse sequence is repeated with the phase encoding pulse 204 stepped through its successive values to acquire an array of complex MR signal samples that comprise the data set of slices.

An alternating magnetic field gradient is applied after the transverse magnetization is produced and before the MR signal is acquired. In the pulse sequence illustrated in FIG. 2, the read gradient, $G_x$, is used for this function and is alternated in polarity to produce bipolar, gradient waveforms 215. The frequency of the alternating gradient 215 is set to the same frequency used to drive the MRE transducer. At the same time, the pulse sequence server 110 of FIG. 1 produces synchronizing ("sync") pulses 217, which have the same frequency as and have a specific phase relationship with respect to the alternating gradient pulses 215. These sync pulses 217 are used to produce the drive signals for the MRE transducer to apply an oscillating stress 219 to the patient. To insure that the resulting waves have time to propagate throughout the field of view, the sync pulses 217 may be turned on well before the pulse sequence begins, as shown in FIG. 2.

The phase of the MR signal 209 is indicative of the movement of the spins. If the spins are stationary, the phase of the MR signal is not altered by the alternating gradient pulses 215, whereas spins moving along the read gradient axis ("$G_x$-axis") will accumulate a phase proportional to their velocity. Spins which move in synchronism and in phase with the alternating magnetic field gradient 215 will accumulate maximum phase of one polarity, and those which move in synchronism, but 180 degrees out of phase with the alternating magnetic field gradient 215 will accumulate maximum phase of the opposite polarity. The phase of the acquired MR signal 209 is thus affected by the "synchronous" movement of spins along the $G_x$-axis.

The pulse sequence in FIG. 2 can be modified to measure synchronous spin movement along the other gradient axes ($G_y$ and $G_z$). For example, the alternating magnetic field gradient pulses may be applied along the phase encoding axis ("$G_y$-axis") as indicated by dashed lines 221, or they may be applied along the slice select axis ("$G_z$-axis") as indicated by dashed lines 222. Indeed, they may be applied simultaneously to two or three of the gradient field directions to "read" synchronous spin movements along any desired direction.

Referring again to FIG. 1, images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Unfortunately, as described above, some very popular and advantageous pulse sequences, such as an EPI pulse sequence, can inherently present a constant or slowly varying phase ramp when used as part of an MRE pulse sequence. To make matters worse, in some instances, these errors can be vary over time or, when performing three-dimensional (3D) image processing, these errors or discontinuities can produce a high frequency artifact in the slice direction that results in an inaccurate stiffness calculation. When the complex phase difference images are calculated as the complex conjugate product of the complex positively motion encoded image and the complex negatively motion encoded image, these errors persist and are reflected in the wave image. Hence, when the wave image is inverted to create the desired elastogram, the clinical utility of the elastogram is undermined by inaccurate stiffness calculations and other calculations based thereon.

For example a tension, pressure, or shear is applied to a subject and the resulting elongation, compression, or rotation is observed. By measuring the resulting strain, elastic properties of the tissue such as Young's modulus, Poisson's ratio, shear modulus, and bulk modulus can be calculated. Moreover, by applying the stress in all three dimensions and measuring the resulting strain, the elastic properties of the tissue can be completely defined. Similarly, attenuation of the strain wave can be estimated by observing the rate at which the strain decreases as a function of distance from the stress producing source. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications. However, if the wave image includes errors, these errors will persist through each additional calculation.

Figure 3:
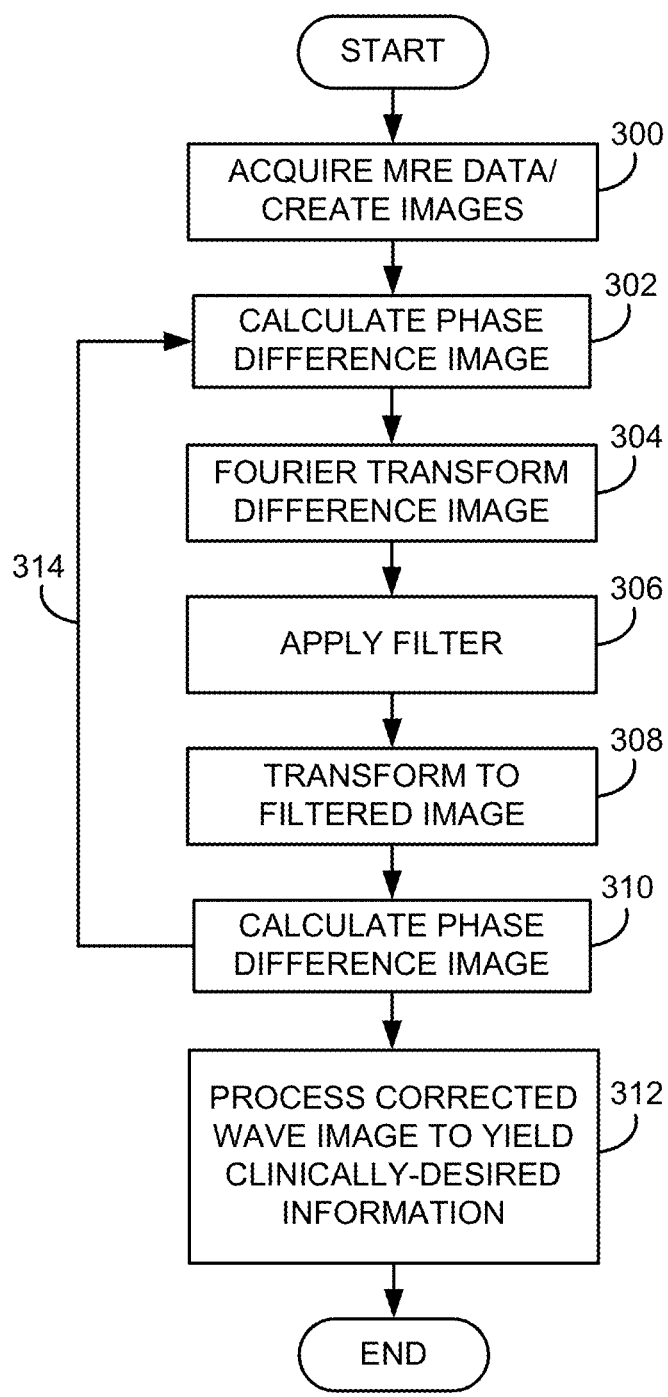
FIG. 3 is a flow chart setting forth the steps of an exemplary method in accordance with the present invention.

Referring to FIG. 3, a flow chart is provided setting forth the steps of a method for providing MRE data or elastograms that do not suffer from errors induced by the use of particular pulse sequences that can result in a constant or slowly varying phase ramp that may remain in the wave image after performing the phase difference calculation and that are different from slice to slice. Specifically, the process begins at process block 300 with the acquisition of MRE data using any of a variety of pulse sequences, including the EPI pulse sequence and variations thereon and the images described above are generated therefrom.

At process block 302, from the acquired data, complex phase difference images may be calculated, such as by the complex conjugate product of the complex positively motion encoded image and the complex negatively motion encoded image. Again, the phase of this image is equal to the phase difference. At process block 304, this complex image is Fourier transformed and, at process block 306, a filter, such as low-pass filter or other filter, is applied in k-space. The low-pass filter may take various forms. For example, the low-pass filter may apply a zeroing everywhere except for a central set of voxels, such as 3×3 set of voxels. These central voxels of the filter may be given a different value, such as a value of one. These are simply exemplary choices and the size of the voxels and whether values other than zero and one may be utilized.

At process block 308, an inverse Fourier transform is applied to yield a filtered image. At process block 310, another complex phase difference image is then calculated as the complex conjugate product of the original complex phase difference image and the filtered complex phase difference image. At process block 312, the phase of this image, now a high-pass filtered result in this example, is processed as corrected wave image to yield the desired elastogram or other calculations based on the corrected wave image.

Thus, in operation, the low passed version of the phase difference image is effectively subtracted off to, thereby, eliminate the ramp artifacts within a slice and produce a stable phase basis for each slice. With all slices being of the same basis, slice direction contributions are thereby eliminated. Accordingly, the present invention corrects for in-plane phase difference errors and slice-to-slice phase difference errors.

It is notable that the above-described method can be performed as an iterative process, such as illustrated by loop 314. That is, the above-described process can be repeated for each acquired slice so that it corrects one slice at a time. In some instances, this can be particularly advantageous because the corrected images have less blurring of the underlying shear waves. Also, this method, in most cases, more completely filters the artifact compared to traditional filtering methods. That is, the above-described method provides various advantages over traditional high-pass or band-pass filters that have been attempted as means to correct errors in the wave image because the present invention can be implemented on a per-slice basis. Thus, the present invention recognizes that gradient or software acquisition errors can be different for each slice and provides a means to correct each slice, if desired, individually rather than only applying a global correction that can still lead to errors in the resulting images and calculations that an undermine the clinical utility of the efforts.

Figures 4A, 4B, 4C:
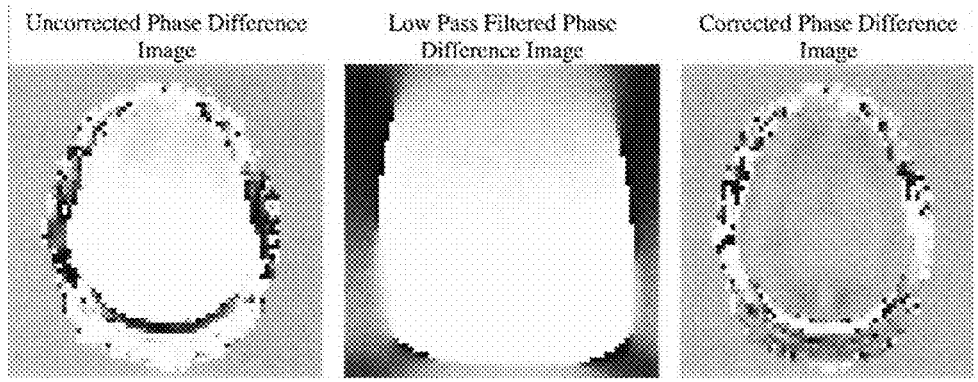
FIG. 4A is an uncorrected phase difference image.
FIG. 4B is a low-pass filtered phase difference image.
FIG. 4C is a corrected phase difference image in accordance with the present invention.

Example images are provided in FIGS. 4A-4C, which shows examples of an original phase difference image (FIG. 4A), a low-pass filtered phase difference image (FIG. 4B), and the corrected phase difference image (FIG. 4C). Even a cursory comparison of FIGS. 4A and 4C shows the striking difference between the two images and illustrates the improved clinical utility of images yielded using the present invention.

Figures 5A, 5B:
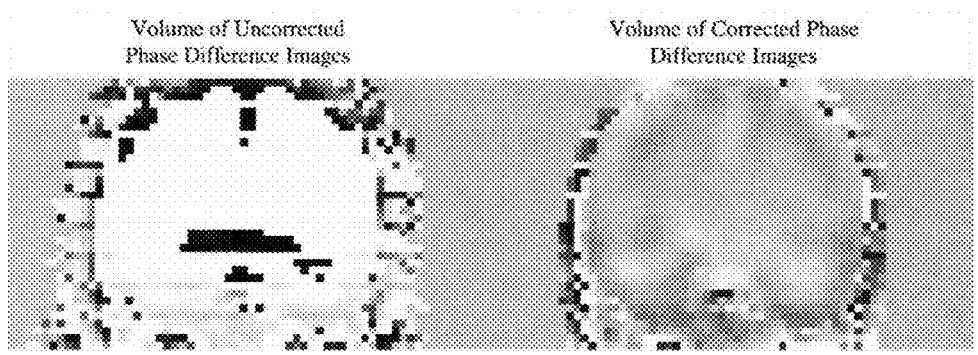
FIG. 5A is a uncorrected volume image illustrating slice discontinuities and artifacts manifesting at a high frequency in the slice direction and resulting in an underestimated stiffness calculation.
FIG. 5B is a corrected volume image of the same volume as illustrated in FIG. 5A showing that the discontinuities are no longer present and the resulting errors in stiffness calculations averted.

Furthermore, FIGS. 5A and 5B provide example volume images before and after correction, respectively. Specifically, the images are a coronal view of a volume of axially acquired phase difference images reformatted so that each line is a slice in the MRE acquisition. In the uncorrected images of FIG. 5A, it is noted the discontinuities indicated as darker horizontal lines compared to surrounding slices. These artifacts have a high frequency in the slice direction resulting in an underestimated stiffness. On the other hand, the volume of FIG. 5B shows the same volume after correction using the proposed method. No discontinuities are present in the corrected volume of FIG. 5B due to the correction of the present invention.

Figure 6A:
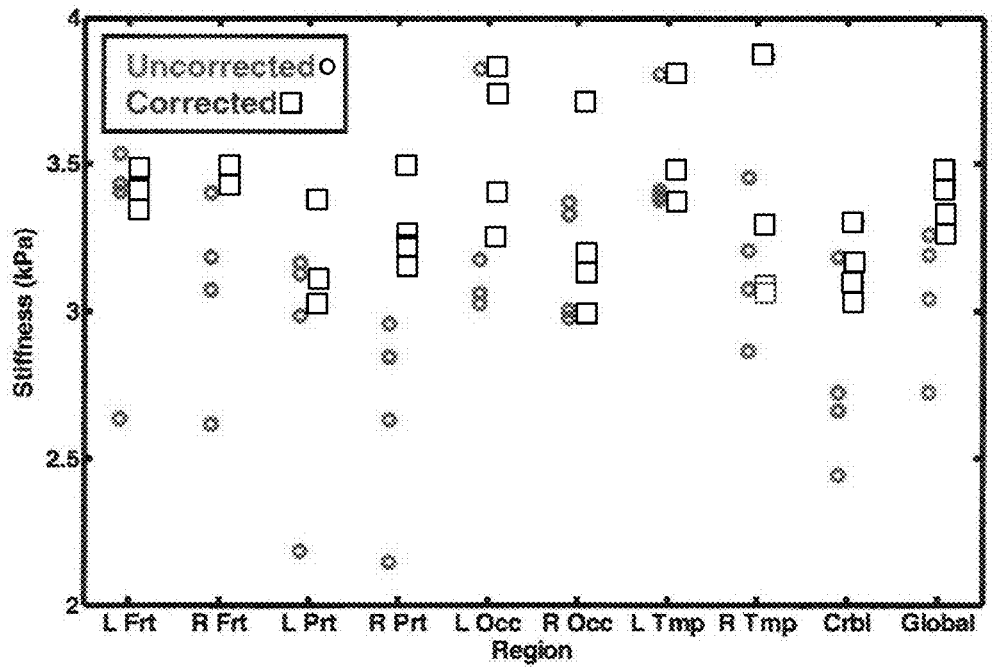
FIGS. 6A and 6B are graphs showing the reproducibility of regional brain stiffness with and without correction.
Figure 6B:
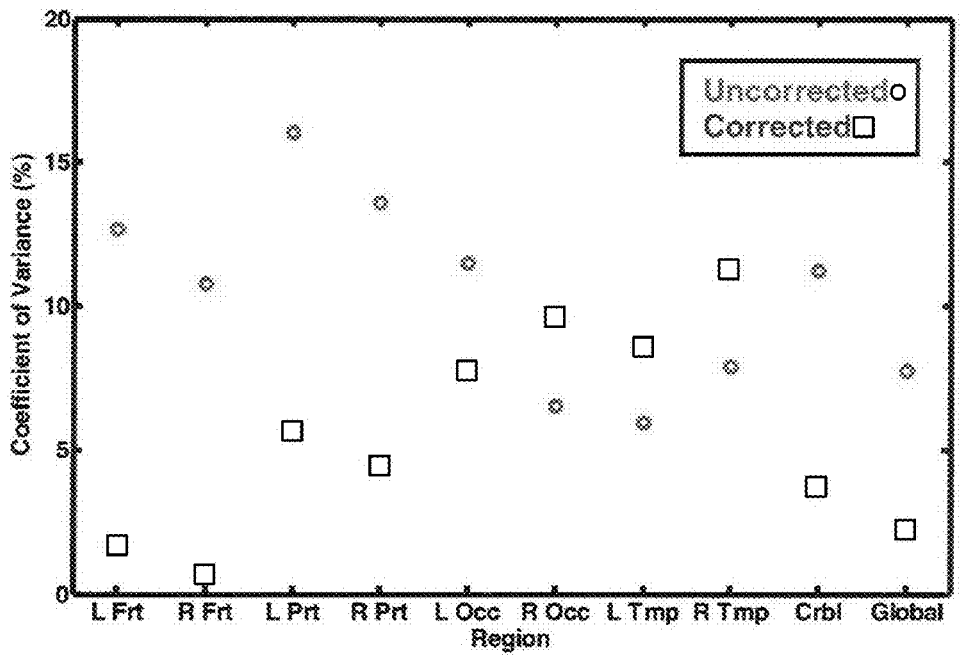

Referring to FIGS. 6A and 6B, the reproducibility of lobar brain stiffness was assessed in a volunteer by performing four MRE exams. The results before and after correction are shown in FIG. 6A. Each marker represents the median stiffness from a region of the brain. Note that the measured stiffness values increase, as expected when removing a high frequency artifact. Also note that, in most cases, the range of the distribution of stiffness measurements is reduced/improved. This result is confirmed in FIG. 6B, which shows the coefficient of variance by region before and after correction. In 7 out of 10 regions, the coefficient of variance decreases. In particular, drastic improvement is observed in the frontal and parietal lobes.

The present invention acts on 2D and 3D slice data to correct for phase artifacts in the phase difference images; and has proven particularly effective for processing MRE volume data. Regardless of the specifics of the implementation for a given application or situation, the present invention provides a system and method whereby the low frequency ramps and offsets can be controlled to be much lower than the waves used in the MRE analysis.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating magnetic resonance elastography (MRE) images:
   a) positioning a subject within an MRI system;
   b) coupling a driver to the subject to impart oscillating energy to the subject;
   c) using the MRI system and in coordination with operation of the driver, performing a pulse sequence having positive and negative motion encoded gradients to acquire positively motion encoded medical imaging data and negatively motion encoded medical imaging data from the subject for a series of slices;
   d) transforming the positively motion encoded medical imaging data and negatively motion encoded medical imaging data for a given slice into a positively encoded medical image and a negatively encoded medical image of the subject;
   e) deriving a difference image from the positively encoded medical image and the negatively encoded medical image;
   f) transforming the difference image into difference medical imaging data;
   g) applying a filter to correct for errors in the difference medical imaging data associated with phase ramps during the pulse sequence and create filtered medical imaging data;
   h) deriving a filtered difference image from the filtered medical imaging data;
   i) generating a corrected difference image from the filtered difference image and the difference image;
   j) repeating steps d) through i) for each lice acquired in step c); and
   k) generating MRE images indicating elastic properties of the subject from the corrected difference image.

2. The method of claim 1 wherein the filter is a low-pass filter applied in k-space.

3. The method of claim 1 wherein the filter is configured to zero the difference medical imaging data outside of a predetermined area in k-space.

4. The method of claim 3 wherein the predetermined area includes a set of predetermined voxels.

5. The method of claim 4 wherein the filter is configured to apply a non-zero value to the predetermined voxels.

6. The method of claim 1 wherein step e) includes calculating a complex phase difference image as a complex conjugate product of the positively encoded medical image and the negatively encoded medical image, the filtered difference image in step h) comprises a filtered complex phase difference image, and step i) includes calculating a second complex phase difference image as a second complex conjugate product of the filtered complex phase difference image and the complex phase difference image.

7. The method of claim 1 wherein step k) includes generating an elastogram.

8. The method of claim 1 wherein the pulse sequence is an echo planar imaging (EPI)-based pulse sequence.

9. A magnetic resonance imaging (MRI) system comprising:
   a magnet system configured to generate a polarizing magnetic field about at least a portion of a subject;
   a plurality of gradient coils configured to apply a gradient field to the polarizing magnetic field;
   a radio frequency (RF) system configured to apply an excitation field to the subject and acquire MR image data therefrom;
   a driver system configured to deliver an oscillatory stress to the subject to, thereby, direct a shear wave through the subject;
   a computer system programmed to:
     a) control operation of the gradient coils and the driver system to coordinate characteristics of the oscillatory stress with application of the gradient field to cycle through positively motion encoding gradients and negative motion encoding gradients;

b) control operation of the RF system to acquire positively motion encoded medical imaging data and negatively motion encoded medical imaging data for a series of slices;
c) derive a difference medical imaging data from the positively encoded medical imaging data and the negatively encoded medical imaging data;
d) apply a filter in k-space to correct for errors in the difference medical imaging data associated with phase ramps during operation of the gradient coils and create filtered medical imaging data;
e) derive filtered difference imaging data from the filtered medical imaging data;
f) generate a corrected difference image from the filtered difference imaging data and the difference imaging data;
g) repeat steps c) through f) for each slice in the series of slices; and
h) generate a report of elastic properties of the subject from the corrected difference image for each slice.

10. The MRI system of claim 9 wherein control of the gradient coils and the RF system is performed according to a echo planar imaging (EPI)-based pulse sequence.

11. The MRI system of claim 9 wherein the filter is a low-pass filter.

12. The MRI system of claim 9 wherein the filter is configured zero the difference medical imaging data outside of a predetermined area in k-space.

13. The MRI system of claim 12 wherein the filter is configured to apply a value of one to voxels in the predetermined area.

* * * * *

UNITED STATES PATENT AND TRADEMARK OFFICE
CERTIFICATE OF CORRECTION

| | | |
|---|---|---|
| PATENT NO. | : 9,134,393 B2 | Page 1 of 1 |
| APPLICATION NO. | : 14/049632 | |
| DATED | : September 15, 2015 | |
| INVENTOR(S) | : Joel P. Felmlee et al. | |

It is certified that error appears in the above-identified patent and that said Letters Patent is hereby corrected as shown below:

In the Specification

Column 1, line 41  -  "process", should be - precess

In the Claims

Column 10, line 24  -  "lice", should be - slice

Column 11, line 27  -  "figured zero", should be - figured to zero

Signed and Sealed this
Nineteenth Day of January, 2016

Michelle K. Lee
*Director of the United States Patent and Trademark Office*